US00PP10577P

United States Patent [19]

Zary

[11] Patent Number: Plant 10,577

[45] Date of Patent: Sep. 1, 1998

[54] FLORIBUNDA ROSE PLANT NAMED 'JACHART'

[75] Inventor: Keith W. Zary, Thousand Oaks, Calif.

[73] Assignee: Bear Creek Gardens, Inc., Medford, Oreg.

[21] Appl. No.: 800,660

[22] Filed: Feb. 14, 1997

[51] Int. Cl.[6] ..... A01H 5/00

[52] U.S. Cl. ..... Plt./24

[58] Field of Search ..... Plt./24

[56] References Cited

U.S. PATENT DOCUMENTS

P.P. 6,953 7/1989 Harkness ..... Plt./24

*Primary Examiner*—Howard J. Locker

*Attorney, Agent, or Firm*—Klarquist Sparkman; Campbell Leigh & Whinston, LLP

[57] ABSTRACT

A new and distinct variety of rose plant of the floribunda class, having strong clustering ability; vigorous upright growth; long stems; fairly large flowers for a spray cut rose; and medium to light yellow flower color.

1 Drawing Sheet

The present invention relates to a new and distinct variety of rose plant of the floribunda class which was originated by me by crossing the variety JACpray (not patented), with the variety HARtanna (U.S. Plant Pat. No. 6,953).

The primary objective of this breeding was to produce a new rose variety having the clustering ability and high cut flower production of the female parent combined with the large flower size and yellow color of the male parent. The objective was substantially achieved, along with other desirable improvements, as evidenced by the following unique combination of characteristics that are outstanding in the new variety and that distinguish it from its parents, as well as from all other varieties of which I am aware:

1. Strong clustering ability;
2. Vigorous, upright growth;
3. Long stems;
4. Fairly large flowers for a spray cut rose;
5. Medium to light yellow flower color.

Asexual reproduction of this new variety by budding, as performed at Wasco, Calif. shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'JACpray'.

*Pollen parent.*—'HARtanna'.

Classification:

*Botanical.*—*Rosa hybrida.*

*Commercial.*—Floribunda.

FLOWER

Observations made from specimens grown in a greenhouse environment at Somis, California from March 1996 to January 1997.

Blooming habit: Recurrent.

Bud:

*Size.*—1-inch long when the petals start to unfurl.

*Form.*—The bud form is long, pointed ovoid.

*Color.*—When sepals first divide, bud color is Yellow Group 5C. When half blown, the upper sides of the petals are Yellow Group 5C; and the lower sides of the petals are Yellow Group 5C.

*Sepals.*—Color: Green Group 138B. Surface texture: Covered in fine hairs. There are three normally appendaged sepals. There are two unappendaged sepals with hairy edges.

*Receptacle.*—Color: Green Group 139C. Shape: Apple. Size: Medium (¼×⅜ inch) Surface: Smooth.

*Peduncle.*—Length: Medium (2½ to 3 inches). Surface: Very glandular. Color: Medium green. Strength: Stiff, erect.

Bloom:

*Size.*—Medium. Average open size is 3½ inches.

*Borne.*—Several together, in clusters of 3–5 flowers.

*Clusters.*—Flat.

*Stems.*—Long and strong. Average length is about 18–22 inches.

*Form.*—When first open: High centered. Permanence: Retains its form to the end.

*Petalage.*—Number of petals under normal conditions: 30–35.

*Color.*—The upper side of the petals is Yellow Group 5C. The reverse side of the petals is Yellow Group 5C. The base of each petal has a small (⅛×⅛ inch) halfmoon of deeper yellow at the point of attachment. The major color on the upper side is Yellow Group 5C.

*Variegations.*—None.

*Discoloration.*—The general tonality at the end of the first day: No change. At the end of the third day: Gradual fading to Yellow Group 5D.

*Fragrance.*—Moderate.

Petals:

*Texture.*—Thick.

*Shape.*—Deltoid.

*Form.*—Tips slightly recurved; edges slightly quilled.

*Arrangement.*—Imbricated, with a few petaloids in the center.

*Persistence.*—Petals drop off cleanly.

*Lastingness.*—On the plant: Fair (5–6 days). As a cut flower: Fair (7–8 days).

Reproductive parts:

*Anthers.*—Size: Medium. Quantity: Many. Color: Yellow. Arrangement: Regular around styles.

*Filaments.*—Color: Yellow.
*Pollen.*—Color: Gold yellow.
*Styles.*—Color: Greenish white.
*Stigmas.*—Color: Greenish white.

Form: Bush.

Growth: Vigorous, upright and branching; height at one year in the greenhouse without pruning is 6–7 feet; width 4 feet. Produces about 150 stems per square meter of greenhouse.

Foliage:

*Number of leaflets on normal mid-stem leaves.*—5 or 7.
*Size.*—Medium (5 inches×3½ inches) Normal.
*Quantity.*—Normal.
*Color.*—New foliage: Greyed Orange Group 174B, quickly becoming green. Old foliage: Upper surface is Green Group 139A; lower surface is Green Group 139C.

Leaflets:

*Shape.*—Pointed oval.
*Texture.*—Upper side: Leathery.
*Edge.*—Serrated.
*Serration.*—Single, small.
*Petiole rachis.*—Color: Green.
*Petiole underside.*—Rough, with prickles.
*Stipules.*—Medium (½inch); serrated, bearded.
*Disease resistance.*—Resistant to mildew under normal growing conditions at Somis, Calif. Not tested for rust and blackspot.

Wood:

*New wood.*—Color: Light green. Bark: Smooth.
*Old wood.*—Color: Green. Bark: Smooth.

Prickles:

*Quantity.*—On main canes from base: Ordinary. On laterals from main canes: Ordinary.
*Form.*—Medium (¼–⅜ inch), hooked slightly downward.
*Color when young.*—Red.

Small Prickles:

*Quantity.*—On main stalks: None. On laterals: None.
*Color.*—Green, brown.

I claim:

1. A new and distinct variety of rose plant of the floribunda class, substantially as herein shown and described, characterized particularly as to novelty by the unique combination of strong clustering ability; vigorous upright growth; long stems; fairly large flowers for a spray cut rose; and medium to light yellow flower color.

* * * * *

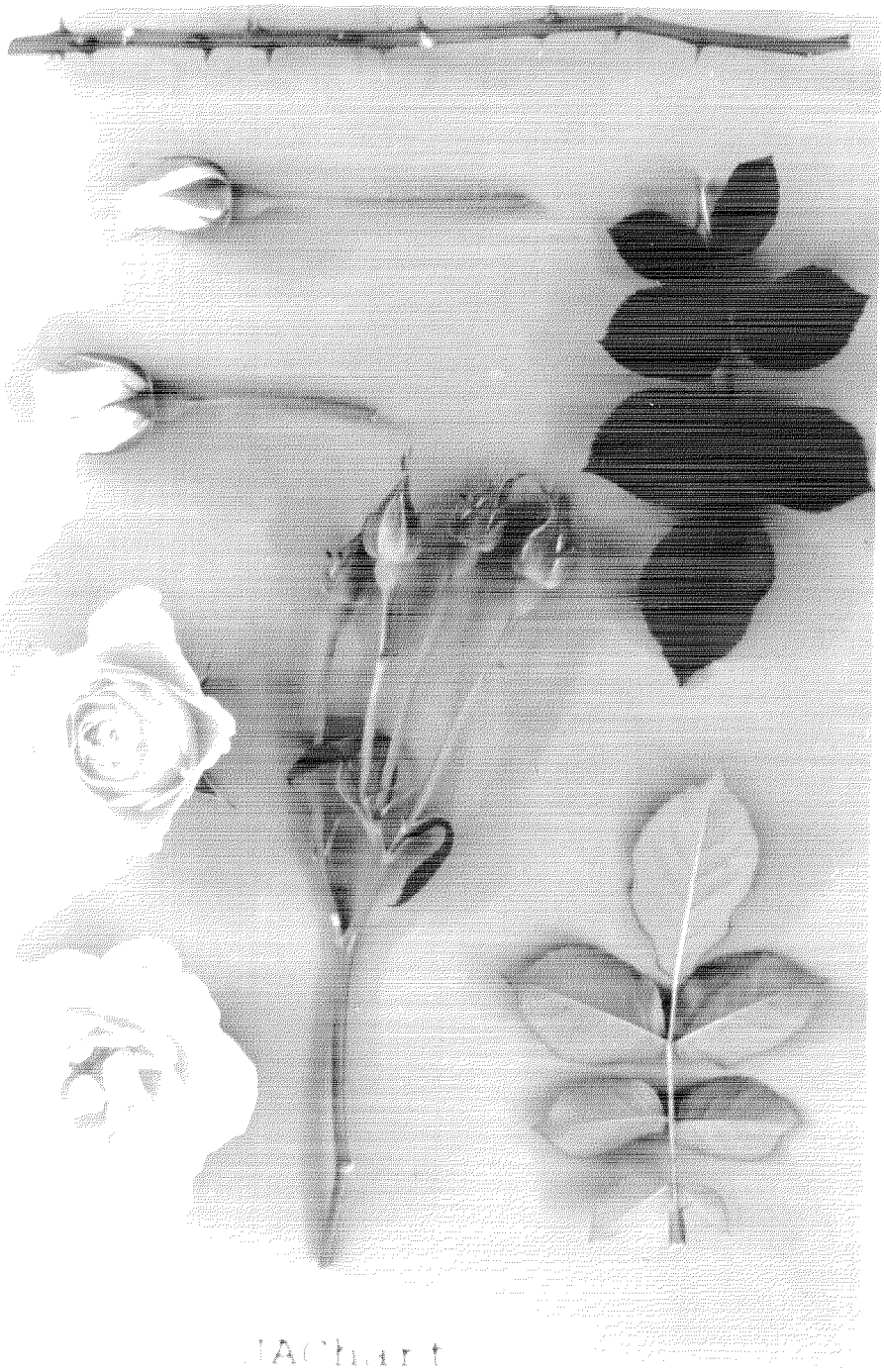

UNITED STATES PATENT AND TRADEMARK OFFICE

CERTIFICATE OF CORRECTION

PATENT NO. : PP 10,577

DATED : September 1, 1998

INVENTOR(S) : Keith Zary

It is certified that error appears in the above-indentified patent and that said Letters Patent is hereby corrected as shown below:

Column 3, line 12, delete "Normal."

Signed and Sealed this

Nineteenth Day of October, 1999

*Attest:*

*Attesting Officer*

Q. TODD DICKINSON

*Acting Commissioner of Patents and Trademarks*